United States Patent
Whitney et al.

(10) Patent No.: US 6,586,711 B2
(45) Date of Patent: Jul. 1, 2003

(54) CURRENT CONTROL METHOD FOR AN OXYGEN SENSOR HEATER

(75) Inventors: Christopher E. Whitney, Milford, MI (US); Yonas Nebiyeloul-Kifle, Braintree, MA (US); Jeffry A. Helmick, Orion, MI (US); Bradley E. De Pottey, Burton, MI (US)

(73) Assignee: General Motors Corporation, Detroit, MI (US)

( * ) Notice: Subject to any disclaimer, the term of this patent is extended or adjusted under 35 U.S.C. 154(b) by 147 days.

(21) Appl. No.: 09/915,479

(22) Filed: Jul. 27, 2001

(65) Prior Publication Data

US 2003/0019865 A1 Jan. 30, 2003

(51) Int. Cl.[7] .................................................. H05B 1/02
(52) U.S. Cl. ........................ 219/497; 219/499; 219/505
(58) Field of Search ................................ 219/209, 492, 219/497, 499, 505; 323/243; 204/408, 421, 424; 60/276; 123/697

(56) References Cited

U.S. PATENT DOCUMENTS

| 4,524,264 A | * | 6/1985 | Takeuchi et al. ............. 219/497 |
| 4,708,777 A | * | 11/1987 | Kuraoka ...................... 204/408 |
| 5,148,795 A | * | 9/1992 | Nagai et al. ................. 123/697 |
| 5,214,267 A | * | 5/1993 | Hoshi et al. ................. 219/497 |

* cited by examiner

Primary Examiner—Tu Ba Hoang
(74) Attorney, Agent, or Firm—Christopher DeVries

(57) ABSTRACT

An improved control for the heater element of a motor vehicle engine exhaust gas oxygen sensor determines the temperature of the heater element and adjusts the heater element current by closed-loop control to minimize deviation of the heater element temperature from a desired heater temperature determined in relation to the desired oxygen sensor temperature. The heater temperature is calculated based on the heater element resistance, and the heater resistance is adaptively adjusted to account for sensor-to-sensor variation. The adaptive adjustment is updated based on a deviation of the measured heater element resistance from an expected value under predetermined calibration conditions at engine start-up.

8 Claims, 3 Drawing Sheets

US 6,586,711 B2

CURRENT CONTROL METHOD FOR AN OXYGEN SENSOR HEATER

TECHNICAL FIELD

This invention relates to a current control for the heater of an exhaust gas oxygen sensor and, more particularly, to a control for maintaining a desired temperature of the oxygen sensor.

BACKGROUND OF THE INVENTION

Motor vehicle exhaust gas emission controls rely almost exclusively on catalytic conversion, and the conversion efficiency is optimized through the use of air/fuel ratio feedback signals developed by exhaust gas oxygen sensors. Since the oxygen sensors only operate in a warmed-up state, it is customary to package the sensors with an integral heater element that is electrically activated following engine start-up to quickly heat up the oxygen sensor and maintain it at or above a desired operating temperature, such as 600° C. However, it is difficult to accurately determine if the oxygen sensor is sufficiently heated without actually measuring the sensor temperature, which would significantly increase the system cost. In some current production vehicles, the engine controller estimates the oxygen sensor temperature by table look-up based on various known system parameters, but such an approach requires a considerable calibration effort, and fails to take into account that the heater element electrical resistance can vary substantially from sensor to sensor. Accordingly, what is needed is an improved method of activating the heater element of an exhaust gas oxygen sensor to ensure accurate and reliable control of the sensor temperature.

SUMMARY OF THE INVENTION

The present invention is directed to an improved control for the heater element of a motor vehicle engine exhaust gas oxygen sensor, wherein the temperature of the heater element is accurately and inexpensively determined, and a closed-loop control of the heater element current minimizes deviations of the heater element temperature from a desired heater temperature determined in relation to the desired oxygen sensor temperature. In a preferred embodiment, the heater temperature is calculated based on the heater element resistance, and the heater element resistance is adaptively adjusted to account for sensor-to-sensor variation. The adaptive adjustment is updated based on a deviation of the measured heater element resistance from an expected value under predetermined calibration conditions at engine start-up.

BRIEF DESCRIPTION OF THE DRAWINGS

FIG. 3 illustrates a routine for determining the temperature of the heater element of FIG. 1B, and FIG. 4 illustrates a routine for periodically adjusting an adaptive offset used in the routine of FIG. 3 according to this invention.

DESCRIPTION OF THE PREFERRED EMBODIMENT

Figure 1A:
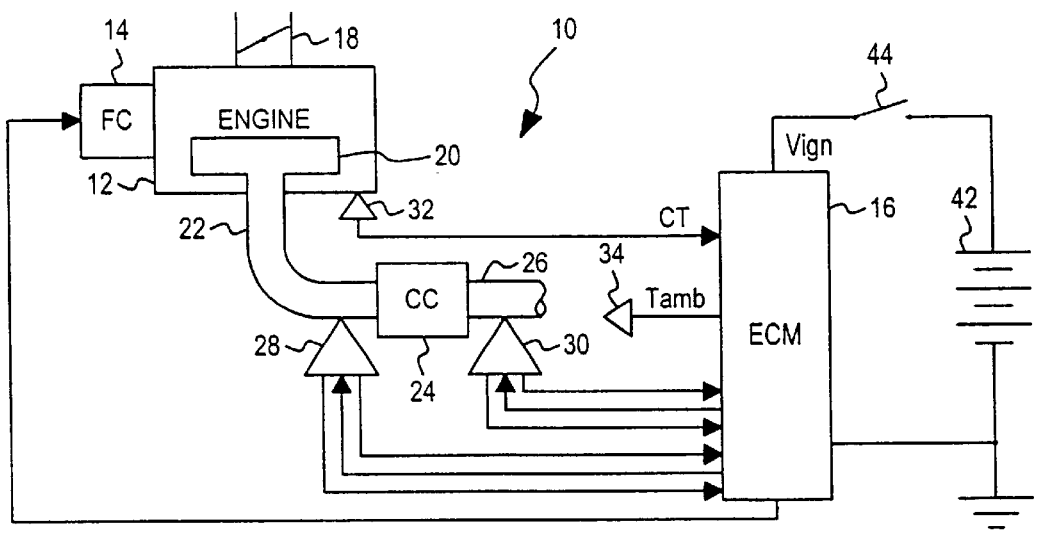
FIG. 1A is a schematic diagram of a vehicle power plant, including an internal combustion engine, exhaust gas oxygen sensors with integral heater elements, and an electronic control module programmed to carry out the control method of this invention.

Referring to the drawings, and particularly to FIG. 1A, the reference numeral 10 generally designates a portion of a vehicle drive train including an internal combustion engine 12 having a conventional fuel control (FC) mechanism 14 operated under the control of a microprocessor-based electronic control module (ECM) 16. Air ingested through throttle 18 is combined with fuel delivered by fuel control mechanism 14 for combustion in engine cylinders (not shown), and the combustion products (exhaust gases) pass through exhaust manifold 20, header pipe 22, catalytic converter 24, and tailpipe 26. Catalytic converter 24 is designed to reduce tailpipe emissions, and provides optimum performance when ECM 16 maintains the engine air/fuel ratio within a specified range. The ECM 16 performs the air/fuel control by analyzing a variety of input signals, including signals produced by a first exhaust gas oxygen sensor 28 located upstream of catalytic converter 24 in header pipe 22 and a second exhaust gas oxygen sensor 30 located downstream of catalytic converter 24 in tailpipe 26. Other pertinent input signals shown in FIG. 1 include an engine coolant temperature signal (CT) and an ambient temperature signal (Tamb), such signals being obtained from suitable temperature sensors 32 and 34, respectively.

Figure 1B:
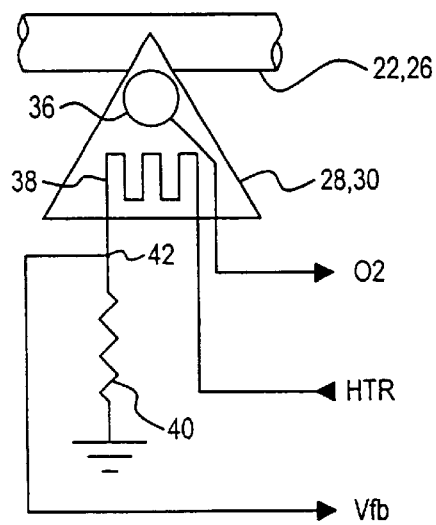
FIG. 1B is a diagram of one of the exhaust gas oxygen sensors of FIG. 1A, illustrating its integral heater element.

FIG. 1B schematically depicts an oxygen sensor representative of the oxygen sensors 28 and 30 of FIG. 1A, and illustrates that each such sensor includes an oxygen sensor element 36 and an integral heater element 38. When the temperature of sensor element 36 is at or above a defined operating temperature, it generates a signal representative of the detected exhaust gas air/fuel ratio, and provides such signal to ECM 16 via the line labeled O2 for fuel control purposes, as mentioned above. One end of the heater element 38 is coupled to ECM 16 via the line labeled HTR, while the other end is coupled to ground through a precision resistor 40. The ECM 16 is coupled to a vehicle storage battery 42 via ignition switch 44, and supplies current to heater 38 via the HTR line and the ground connection of resistor 40. A feedback voltage proportional to the current supplied to heater element 38 by ECM 16 is developed at the junction 46 between heater element 38 and resistor 40, and the line labeled Vfb provides such voltage to ECM 16 for purposes of measuring the heater element current.

As indicated above, the method of this invention is principally directed to a current control for a respective heater element 38 that inexpensively and reliably maintains the associated oxygen sensor element 36 at or above a desired operating temperature such as 600° C. The control involves determining the temperature of the heater element based on its resistance, and controlling the heater element current by closed-loop to minimize the deviation (error) of the heater element temperature from a desired heater temperature determined in relation to the desired oxygen sensor temperature. For example, the oxygen sensor element 36 may be reliably maintained at or above 600° C. by reliably maintaining the heater element temperature at a suitably higher temperature, such as 850° C. According to the invention, the heater temperature is calculated based on the heater element resistance, and the heater element resistance is adaptively adjusted to account for sensor-to-sensor variation, the adaptive adjustment being updated based on a deviation of the measured heater element resistance from its nominal value under predetermined calibration conditions at engine start-up.

Figure 2:
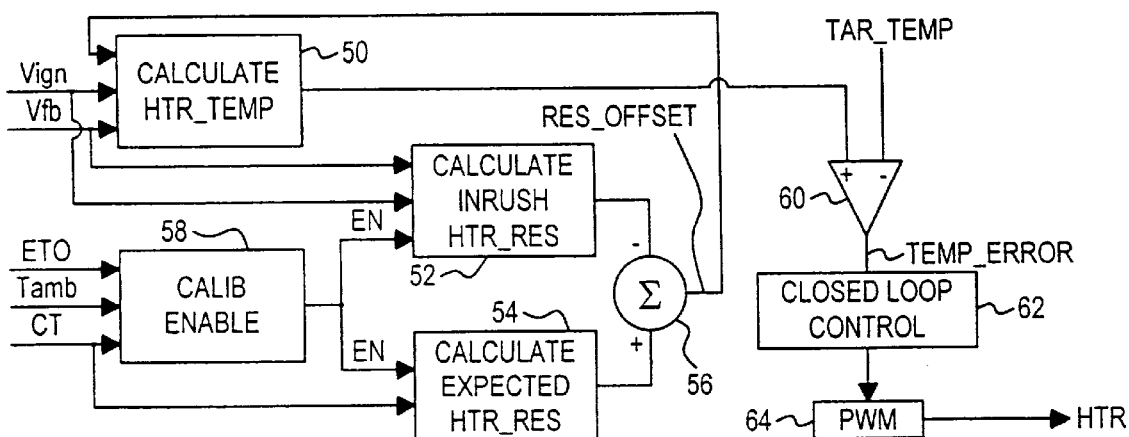
FIG. 2 is a block diagram illustrating the control of this invention.

The block diagram of FIG. 2 generally illustrates the control of this invention. The block 50 calculates the heater element temperature HTR_TEMP, the blocks 52, 54 and 56 update the adaptive adjustment (RES_OFFSET) when enabled by Calibration Enable block 58, and the blocks 60, 62 and 64 develop a closed-loop heater current command. In general, the heater element temperature HTR TEMP may be calculated based on the heater element resistance HTR_RES according to the equation:

$$HTR\_TEMP=TEMP\_RT+(HTR\_RES-RES\_RT)*DEG\_PER\_OHM \quad (1)$$

where TEMP_RT is a standard room temperature such as 20° C., RES_RT is the nominal heater element resistance at room temperature, and DEG_PER_OHM is a temperature vs. resistance relationship specified by the manufacturer of the heater element. However, as mentioned above, the calculation performed by block 50 according to this invention also involves an adaptive offset (RES_OFFSET) to the nominal heater element resistance HTR_RES, as shown in the following equation:

$$HTR\_TEMP=TEMP\_RT+(HTR\_RES+RES\_OFFSET-RES\_RT)*DEG\_PER\_OHM \quad (2)$$

The heater element resistance HTR RES in this case is determined by the equation:

$$HTR\_RES=V\_IGN/HTR\_CURRENT \quad (3)$$

where V_IGN is the ignition voltage Vign shown in FIG. 1A, and HTR_CURRENT is a measure of the heater element current based on the feedback voltage on line Vfb of FIG. 1B. The adaptive offset (RES_OFFSET) is adjusted during a calibration period at engine start-up where the engine 12 has been off for at least a predetermined time period such as five hours, and the engine coolant temperature CT is substantially equal to the ambient temperature Tamb. Thus, Calibration Enable block 58 is responsive to CT, Tamb and an engine time off variable ETO. When calibration is enabled, the block 52 calculates the heater element resistance using equation (3), and block 54 calculates the heater element resistance with equation (1), rearranged as follows:

$$HTR\_RES=RES\_RT+(HTR\_TEMP-TEMP\_RT)/(DEG\_PER\_OHM) \quad (4)$$

and assuming that the heater element temperature HTR_TEMP is the same as the engine coolant temperature CT. The heater resistance calculated by block 52 is considered to be the actual heater resistance, whereas the heater resistance calculated by block 54 is considered to be the expected heater resistance, and their difference is determined at summer block 56 to form the resistance offset RES_OFFSET supplied to block 50.

The heater element temperature output HTR_TEMP of block 50 is supplied as an input, along with the target heater element temperature TAR_TEMP (which may be 850° C., for example), to error amplifier block 60, which develops the temperature error TEMP_ERROR. The closed-loop control block 62, which may be a conventional PI or PID control, is responsive to TEMP_ERROR, and develops a control signal for PWM block 64, which in turn, is coupled to the oxygen sensor heater line HTR. In this way, the heater element current is controlled to minimize TEMP_ERROR, maintaining the heater element temperature at TAR_TEMP.

Figure 3:
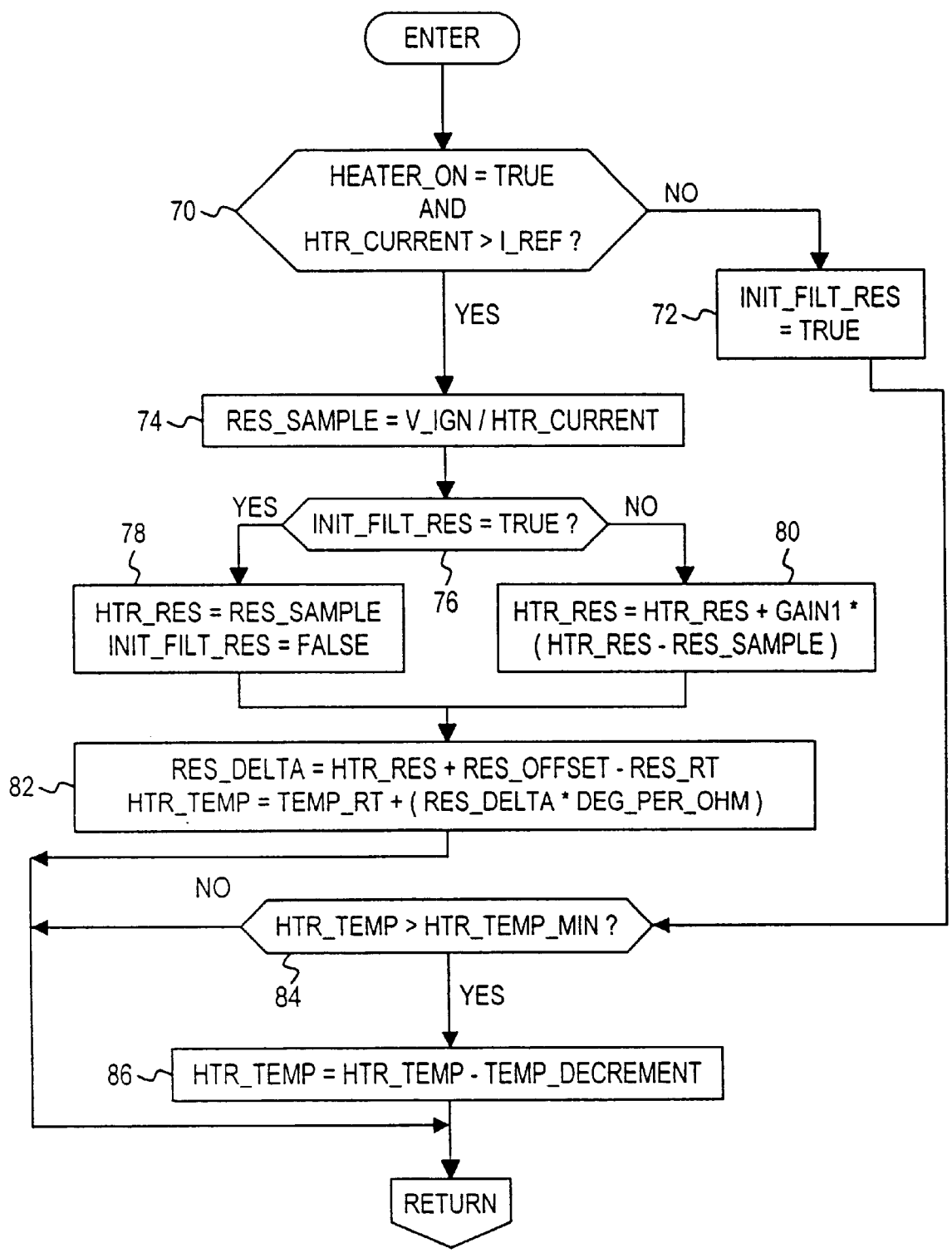
FIGS. 3 and 4 are flow diagrams representative of computer program instructions executed by the electronic control module of FIG. 1 in carrying out the control of this invention.
Figure 4:
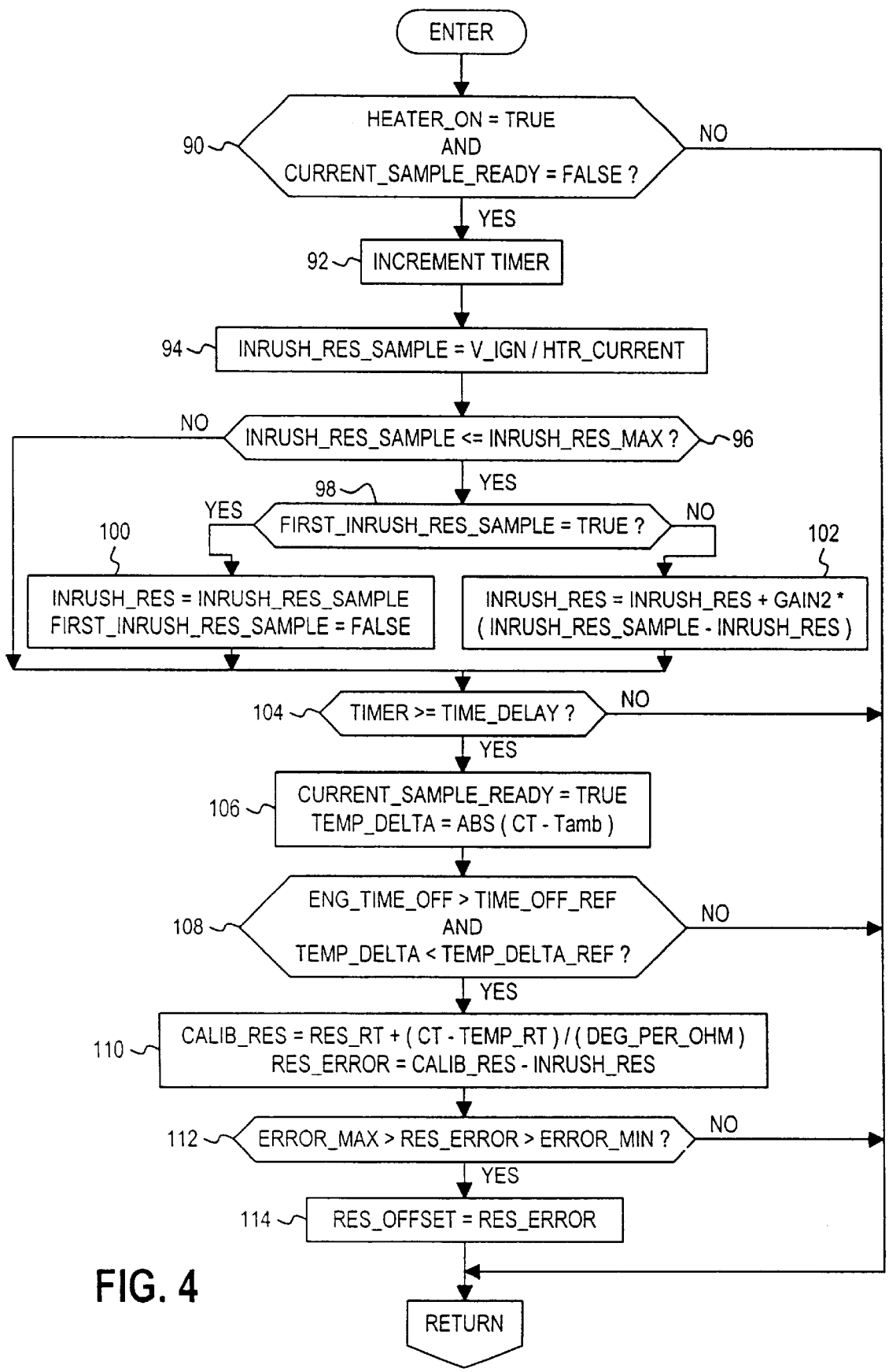

The flow diagrams of FIGS. 3–4 illustrate computer software routines executed by ECM 16 of FIG. 1 for carrying out the functionality of blocks 50–58. The flow diagram of FIG. 3 illustrates the functionality of block 50, while the flow diagram of FIG. 4 illustrates the functionality of blocks 52–58. Each of the illustrated routines is periodically executed during the course of engine operation, and a main or executive routine initializes the various parameters and variables utilized by the routines, as mentioned below.

Referring to the flow diagram of FIG. 3, the block 70 is initially executed to determine if the heater element 38 is on and the heater current (that is, the feedback voltage divided by the resistance of resistor 40) is at least as large as a reference current I REF, such as 0.5 amps. If the conditions are not met, block 72 sets the INIT_FILT_RES flag to true, and the blocks 84 and 86 decrement the estimated heater temperature HTR TEMP toward a minimum value HTR_TEMP_MIN, completing the routine. The INIT_FILT_RES flag is tested at block 76, and indicates when true that the heater resistance variable HTR_RES needs to be initialized. If block 70 is answered in the affirmative, the block 74 calculates a heater element resistance sample RES_SAMPLE using equation (3), and if block 76 reveals that the INIT_FILT_RES flag is true, the block 78 sets HTR_RES equal to RES_SAMPLE and sets the INIT_FILT_RES flag to false. In subsequent execution of the routine, block 76 will be answered in the negative, and block 80 will use a first-order filter equation to update HTR_RES based on the latest value of RES_SAMPLE; referring to block 80, GAIN1 is simply a predefined filter gain term. Once the heater element resistance HTR_RES has been determined, the block 82 computes the corresponding heater element temperature HTR_TEMP using equation (3); for ease of notation, block 82 defines an intermediate variable RES_DELTA as indicated.

Referring to the flow diagram of FIG. 4, the block 90 is initially executed to determine if the heater element 38 is on and the CURRENT_SAMPLE_READY flag is false. The CURRENT_SAMPLE_READY flag is initialized to the false state so that block 90 is answered in the affirmative as soon as the heater element 38 is turned on following engine start-up. When block 90 is answered in the affirmative, the block 92 increments a timer for measuring the on-time of the heater element, and blocks 94, 96, 98, 100, 102, 104 are executed to determine the heater element resistance INRUSH_RES based on the filtered heater current over a predetermined interval after turn-on. The block 94 computes a heater element resistance sample INRUSH_RES_SAMPLE using equation (3). So long as INRUSH_RES_SAMPLE is less than a maximum value INRUSH_RES_MAX, as determined at block 96, the blocks 100 or 102 compute INRUSH_RES. The FIRST_INRUSH_RES_SAMPLE flag, checked at block 98, is initialized to true so that block 100 is executed in the first pass through the routine to initialize the INRUSH_RES filter. As indicated, this involves setting INRUSH_RES equal to the resistance sample INRUSH_RES_SAMPLE and setting the FIRST_INRUSH_RES_SAMPLE flag to false. In a subsequent execution of the routine, block 98 will be answered in the negative, and block 102 will use a first-order filter equation to update INRUSH_RES based on the latest value of INRUSH_RES_SAMPLE; referring to block 102, GAIN2 is simply a predefined filter gain term. When the timer has been incremented to a reference interval TIME_DELAY as determined by block 104, the blocks 106 and 108 are executed to set the CURRENT_SAMPLE_READY flag to true, and to determine if calibration of the RES_OFFSET should be enabled. Setting the CURRENT_SAMPLE_READY flag to true ensures that block 90 will thereafter be answered in the negative so that further execution of the routine will be prevented until the next engine start-up. The block 106 also computes the magnitude TEMP_DELTA of the difference (CT _Tamb), and the block 108 only enables calibration of RES_OFFSET if the engine time off ENG_TIME_OFF (ETO in FIG. 2) exceeds a reference such as five hours and TEMP_DELTA is less than a reference temperature TEMP_DELTA_REF, such as 5° C. If the calibration enable conditions are not met, the routine is exited; if the conditions are met, the blocks 110, 112, 114 are executed to update RES_OFFSET. The block 110 computes a calibration heater resistance CALIB_RES using equation (4), and calculates the resistance error RES_ERROR according to the difference (CALIB_RES−INRUSH_RES). So long as RES_ERROR is between minimum and maximum values ERROR_MIN, ERROR_MAX, as determined at block 112, the block 114 sets the resistance offset RES_OFFSET equal to RES_ERROR, completing the routine.

In summary, the control of this invention provides a reliable and cost-effective way of efficiently maintaining a heated oxygen sensor at a desired operating temperature. While described in reference to the illustrated embodiment, it is expected that various modifications in addition to those mentioned above will occur to those skilled in the art. For example, various current control strategies such as a discrete dead-band control can be used in place of the illustrated PWM control, and so on. Also, a temperature prediction algorithm may be used in place of the described heater temperature calculation (block 50 in FIG. 2, flow diagram of FIG. 3); in such case, the predicted heater temperature can be modified based on the offset term RES_OFFSET to compensate for heater resistance variations. Thus, it will be understood that the scope of this invention is not limited to the illustrated embodiment, and that controls incorporating such modifications may fall within the scope of this invention, which is defined by the appended claims.

What is claimed is:

1. A method of operation for an exhaust gas oxygen sensor of a motor vehicle engine, the sensor having an integral heater element that is supplied with electric current to heat the sensor to a desired operating temperature, the method comprising the steps of:

estimating a temperature of the heater element based on an electrical resistance parameter for said heater element;

establishing a target temperature of said heater element for heating said oxygen sensor to said desired operating temperature;

supplying electric current to said heater element based on a deviation of said estimated temperature from said target temperature so as to drive said estimated temperature into correspondence with said target temperature; and adaptively updating said electrical resistance parameter to compensate said estimated temperature for deviation of an actual electrical resistance of said heater element from an expected electrical resistance of said heater element.

2. The method of operation of claim 1, including the steps of:

calculating an electrical resistance of said heater element;

determining said electrical resistance parameter based on said calculated electrical resistance and an offset resistance; and adaptively updating said offset resistance based on the deviation of the actual electrical resistance of said heater element from the expected electrical resistance of said heater element.

3. The method of claim 2, wherein the step of calculating said electrical resistance includes the steps of:

periodically calculating electrical resistance samples; and calculating said electrical resistance by filtering said electrical resistance samples.

4. The method of claim 1, including the step of:

progressively reducing the estimated temperature of said heater element when the electrical current supply to said heater element is interrupted.

5. The method of claim 1, wherein the expected electrical resistance of said heater element is determined based on a coolant temperature of said engine, and the step of adaptively updating said electrical resistance parameter is enabled upon commencement of a period of operation of said engine if said engine had been inoperative for at least a predefined interval of time prior to the commencement of said period of operation.

6. The method of claim 5, wherein the step of adaptively updating said electrical resistance parameter is enabled upon commencement of a period of operation of said engine if said engine had been inoperative for at least a predefined interval of time prior to the commencement of said period of operation and said coolant temperature is substantially equal to an ambient air temperature.

7. The method of claim 5, wherein the step of adaptively updating said electrical resistance parameter including the steps of:

calculating the actual electrical resistance of said heater element based on the electrical current supplied to said heater element; and calculating the expected electrical resistance of said heater element based on said coolant temperature; and adaptively updating said electrical resistance parameter based on a deviation of the calculated actual electrical resistance from the calculated expected electrical resistance.

8. The method of claim 7, wherein the step of calculating said actual electrical resistance includes the steps of:

periodically calculating actual electrical resistance samples based on the supplied electrical current and a supply voltage; and calculating said actual electrical resistance by filtering the calculated actual electrical resistance samples over an initial interval of current supply to said heater element.

* * * * *